United States Patent
Nakayama et al.

(10) Patent No.: US 7,126,677 B2
(45) Date of Patent: Oct. 24, 2006

(54) BEARING WITH OIL FILM THICKNESS MEASURING DEVICE

(75) Inventors: Kei Nakayama, Inuyama (JP); Takeshi Katagiri, Inuyama (JP); Yutaka Okamoto, Inuyama (JP); Takayuki Shibayama, Inuyama (JP)

(73) Assignee: Daido Metal Company Ltd., Nagoya (JP)

( * ) Notice: Subject to any disclaimer, the term of this patent is extended or adjusted under 35 U.S.C. 154(b) by 177 days.

(21) Appl. No.: 10/342,609

(22) Filed: Jan. 15, 2003

(65) Prior Publication Data

US 2003/0160973 A1    Aug. 28, 2003

(30) Foreign Application Priority Data

Feb. 27, 2002   (JP) .............................. 2002-051465

(51) Int. Cl.
*G01B 11/26* (2006.01)
*G01B 11/06* (2006.01)

(52) U.S. Cl. ...................... 356/70; 356/138; 356/632; 250/559.3

(58) Field of Classification Search ................. 356/70, 356/630, 632, 301, 138; 250/301, 559.27, 250/559.28, 557.3
See application file for complete search history.

(56) References Cited

U.S. PATENT DOCUMENTS

| | | | | |
|---|---|---|---|---|
| 4,956,558 A | * | 9/1990 | Batishko et al. ............ | 250/301 |
| 4,978,850 A | * | 12/1990 | Nakamura et al. ..... | 250/227.11 |
| 5,155,402 A | * | 10/1992 | Bichler ...................... | 310/90.5 |
| 6,075,611 A | * | 6/2000 | Dussan V. et al. .......... | 356/436 |

* cited by examiner

*Primary Examiner*—Richard A. Rosenberger
(74) *Attorney, Agent, or Firm*—Rader, Fishman & Grauer PLLC

(57) ABSTRACT

A bearing with an oil film thickness measuring device in which sensor portions at distal ends of four common optical fibers are connected to sensor mounting portions formed at four positions in an axial direction of a bearing body. A lubricating oil containing a fluorescent agent is supplied to a sliding surface of the bearing body. A laser beam generated from a laser beam generator is branched into four beams, which are applied to an oil film on a sliding surface through each of sensor portions. Fluorescence generated by the fluorescent agent in the oil film, passing through a return-route optical fiber, is introduced into a photomultiplier tube, and is detected. Since the fluorescence intensity detected by the photomultiplier tube is proportional to the thickness of oil film, the absolute value of oil film thickness can be measured. In this case, the oil film thickness can be measured at four positions.

4 Claims, 6 Drawing Sheets

(THE CENTER OF BEARING LENGTH)

THE MEASUREMENT POSITIONS
IN THE AXIAL DIRECTION (THE CENTER OF BEARING LENGTH)
THE MEASUREMENT POSITIONS
IN THE AXIAL DIRECTION (THE CENTER OF BEARING LENGTH)
THE MEASUREMENT POSITIONS
IN THE AXIAL DIRECTION

BEARING WITH OIL FILM THICKNESS MEASURING DEVICE

CROSS-REFERENCE TO RELATED APPLICATIONS

This application claims priority based on Japanese Application No. 2002-051465, filed Feb. 27, 2002.

FIELD OF THE INVENTION

The present invention relates to a bearing with an oil film thickness measuring device which measures a thickness of an oil film formed on a sliding surface.

BACKGROUND OF THE INVENTION

Conventionally, as a method of measuring a thickness of an oil film formed on a sliding surface of, for example, a bearing, a capacitance type device, an eddy current type device, or the like have been used. However, in these methods, because of a drawback in that although the measurement accuracy of displacement is high, the zero point (origin) drifts, the absolute value of an oil film thickness cannot be measured.

SUMMARY OF THE INVENTION

The present invention has been achieved in view of the above situations, and accordingly an object thereof is to provide a beating with an oil film thickness measuring device capable of measuring the absolute value of an oil film thickness.

To attain the above object, the invention according to claim 1 is characterized by providing a bearing with an oil film thickness measuring device, which has a bearing body for supporting a shaft via an oil film and the oil film thickness measuring device for measuring the thickness of the oil film formed on the sliding surface of the bearing body, wherein a fluorescent agent which generates fluorescence of a predetermined wavelength is mixed in a lubricating oil, and a sensor mounting portion is provided in the bearing body, and the oil film thickness measuring device comprises laser beam generating means for generating a laser beam with a wavelength different from the wavelength of the fluorescence; an approach-route optical fiber having one end of which is connected to the sensor mounting portion and for applying the laser beam generated from the laser beam generating means to an oil film on the sliding surface of the bearing body; a return-route optical fiber having one end of which is connected to the sensor mounting portion and for receiving the fluorescence generated by the fluorescent agent in the oil film according to the application of the laser beam and introducing it to the outside; and fluorescence intensity detecting means for detecting the intensity of fluorescence passing through the return-route optical fiber, whereby the thickness of oil film on the sliding surface is measured based on the detection result of the fluorescence intensity detecting means.

In the above-described configuration, when the thickness of an oil film formed on the sliding surface is measured, a laser beam is generated from the laser beam generating means of the oil film thickness measuring device. Then, the laser beam passes through the approach-route optical fiber and is applied to the oil film on the sliding surface of the bearing body. Based on the application of the laser beam, fluorescence is generated by the fluorescent agent in the oil film. The fluorescence generated by the fluorescent agent passes through the return-route optical fiber and is introduced into the fluorescence intensity detecting means. The fluorescence intensity detecting means detects the intensity of fluorescence having passed through the return-route optical fiber.

At this time, the quantity of fluorescent agent in the oil film is proportional to the thickness of oil film, and the intensity of the fluorescence generated from the fluorescent agent is also proportional to the thickness of oil film. Therefore, the absolute value of oil film thickness can be measured based on the detection result of fluorescence intensity detecting means that detects the fluorescence intensity. According to the bearing configured as described above, this result can be utilized for the maintenance, checking etc. of the bearing.

Also, according to the above-described oil film thickness measuring device, since an optical fiber is used in the sensor portion, the sensor mounting portion takes up less mounting space, and also the degree of freedom of mounting position is high. Further, because of transmission by light, an advantage of being not affected by electrical noise is offered.

The invention according to claim 2 has such a feature that the approach-route optical fiber and the return-route optical fiber are made common by one optical fiber at a point near the sensor mounting portion. According to this configuration, since one optical fiber has only to be connected to the sensor mounting portion, the sensor mounting portion can be made further smaller.

The invention according to claim 3 has such a feature that in the invention according to claim 2, an optical filter that shuts off the passage of a beam with a wavelength other than the wavelength corresponding to the fluorescence is provided on the inlet side of the fluorescence intensity detecting means.

According to this configuration, since the passage of a beam with a wavelength other than the wavelength corresponding to the fluorescence is shut off by the optical filter, only the fluorescence generated by the fluorescent agent is applied to the fluorescence intensity detecting means, so that the fluorescence intensity can be detected properly, and hence the oil film thickness can be measured as exactly as possible.

The invention according to claim 4 has such a feature that the bearing body has the sensor mounting portion at a plurality of positions, and the oil film thickness measuring device has a plurality of sets of the approach-route optical fiber and the return-route optical fiber which are connected to the sensor mounting portion.

According to this configuration, the oil film thickness can be measured at a plurality of positions on the bearing body.

The invention according to claim 5 has such a feature that in the invention according to claim 4, the sensor mounting portion is provided at a plurality of positions in the axial direction of the bearing body.

According to this configuration, the tilting state of the bearing body with respect to the shaft can be detected.

PREFERRED EMBODIMENTS OF THE INVENTION

One embodiment of the present invention will now be described with reference to the accompanying drawings.

Figure 5A:
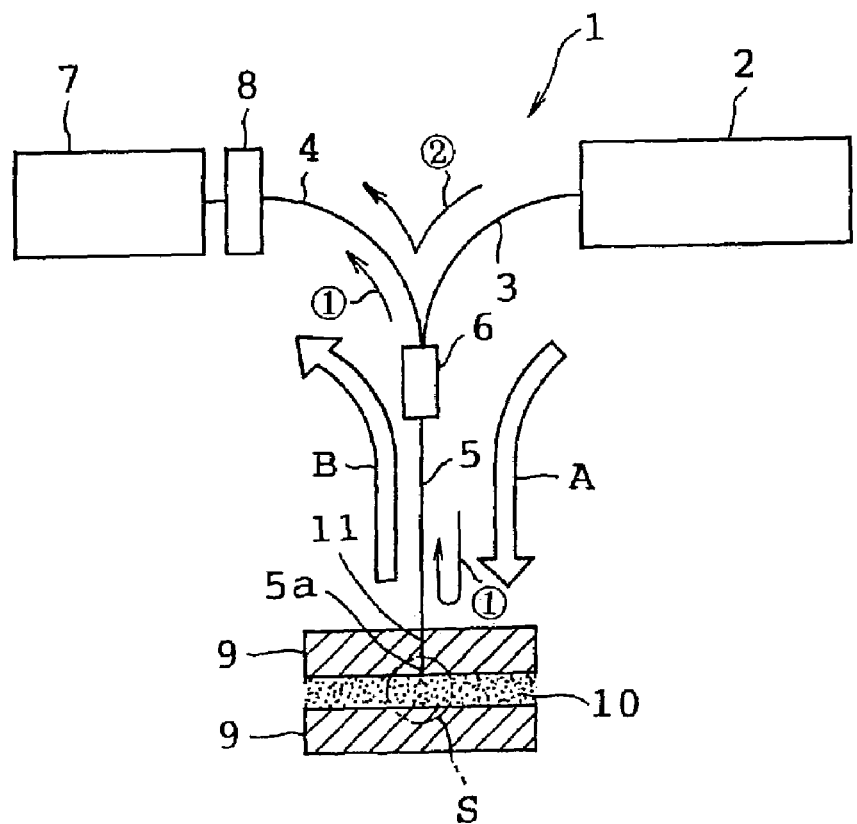
FIG. 5A is a general schematic view showing a measurement principle of an oil film thickness measuring device.
Figure 5B:
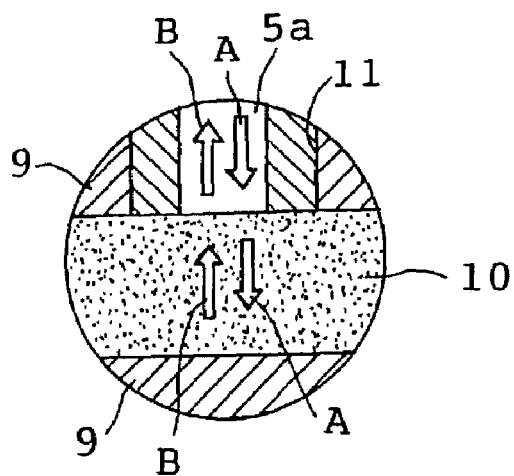
FIG. 5B is an enlarged sectional view of portion S in FIG. 5A.

First, a measurement principle of an oil film thickness measuring device will be described with reference to FIGS. 5A and 5B. In FIG. 5A, an oil film thickness measuring device 1 includes a laser beam generator 2 constituting laser beam generating means, an approach-route optical fiber 3, a return-route optical fiber 4, a common optical fiber 5 which is used as both an approach-route optical fiber and a return-route optical fiber, an optical fiber coupler 6 which connects the approach-route optical fiber 3, the return-route optical fiber 4, and the common optical fiber 5 in a Y shape, a photomultiplier tube 7 constituting fluorescence intensity detecting means, and an optical filter 8 provided on the inlet side of the photomultiplier tube 7.

The laser beam generator 2, which is a He—Cd laser generator in this case, generates a laser beam with a wavelength of 442 nm. The optical filter 8 is a 500 nm band pass filter which allows the passage of only a beam of ±10 nm with respect to 500 nm that is a wavelength of the later-described fluorescence and shuts off the passage of a beam other than the above-described beam. The photomultiplier tube 7 detects the intensity of beam passing through the optical filter 8. The aforementioned optical fibers 3, 4 and 5 have a core diameter of 50 μm. Among these optical fibers, the common optical fiber 5 has a distal end portion serving as a sensor portion Sa.

On the other hand, a fluorescent agent is mixed in advance in a lubricating oil to be measured. As the fluorescent agent, for example, Coumarin 540 (trade name) is used. This fluorescent agent generates fluorescence with a maximum fluorescence wavelength of 500 nm. The concentration of the fluorescent agent in the lubricating oil is set at $5 \times 10^{-4}$ mol/l. The lubricating oil containing this fluorescent agent is held between two metallic plates 9, 9, and an oil film 10 is formed between these metallic plates 9, 9. Of these two metallic plates 9, the metallic plate 9 on the upside in the drawing is formed with a sensor mounting portion 11 (see FIG. 5B) consisting of a through hole penetrating in the thickness direction, and the sensor portion 5a of the common optical fiber 5 is inserted in and connected to the sensor mounting portion 11.

In the above-described configuration, when the thickness of the oil film 10 is measured, a laser beam A with a wavelength of 442 nm is generated from the laser beam generator 2. Then, the laser beam A, passing through the approach-route optical fiber 3, the optical fiber coupler 6, and the common optical fiber 5, is applied to the oil film 10 through the sensor portion 5a as indicated by an arrow mark (see FIG. 5B). Based on the application of the laser beam A, fluorescence B is generated by the fluorescent agent in the oil film 10. The fluorescence B, passing through the common optical fiber 5, the optical fiber coupler 6, the return-route optical fiber 4, and the optical filter 8, is introduced into the photomultiplier tube 7 as indicated by an arrow mark.

At this time, of the laser beam A, a beam reflected by a measurement surface (surface of the oil film 10) as indicated by a route <1> in FIG. 5A and a beam reflected by the optical fiber coupler 6 as indicated by a route <2> are also directed toward the photomultiplier tube 7 as an unnecessary light. However, since the optical filter 8 consisting of a 500 nm band pass filter is provided on the inlet side of the photomultiplier tube 7, only a beam of ±10 nm with respect to the wavelength of 500 nm of the fluorescence B passes through the optical filter 8 and is introduced into the photomultiplier tube 7, and the laser beam A, which is a beam deviated from this wavelength, is inhibited from passing through the optical filter 8. As a result, the intensity of only the fluorescence B, which has passed through the optical filter 8, is detected by the photomultiplier tube 7.

In this case, the quantity of fluorescent agent in the oil film 10 is proportional to the thickness of the oil film 10, and the intensity of the fluorescence B generated from the fluorescent agent is also proportional to the thickness of the oil film 10. Therefore, the measurement of only the intensity of the fluorescence B corresponding to the thickness of the oil film 10 by means of the photomultiplier tube 7 enables the measurement of the absolute value of the thickness of the oil film 10.

Figure 6:
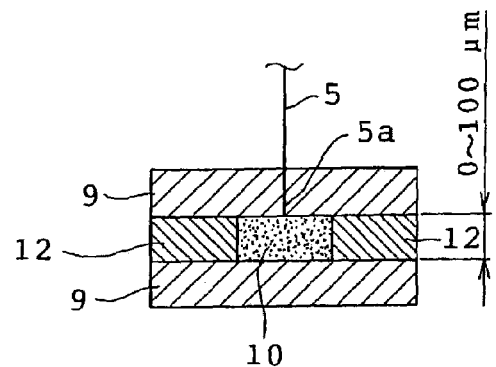
FIG. 6 is a sectional view for illustrating a calibration method.
Figure 7:
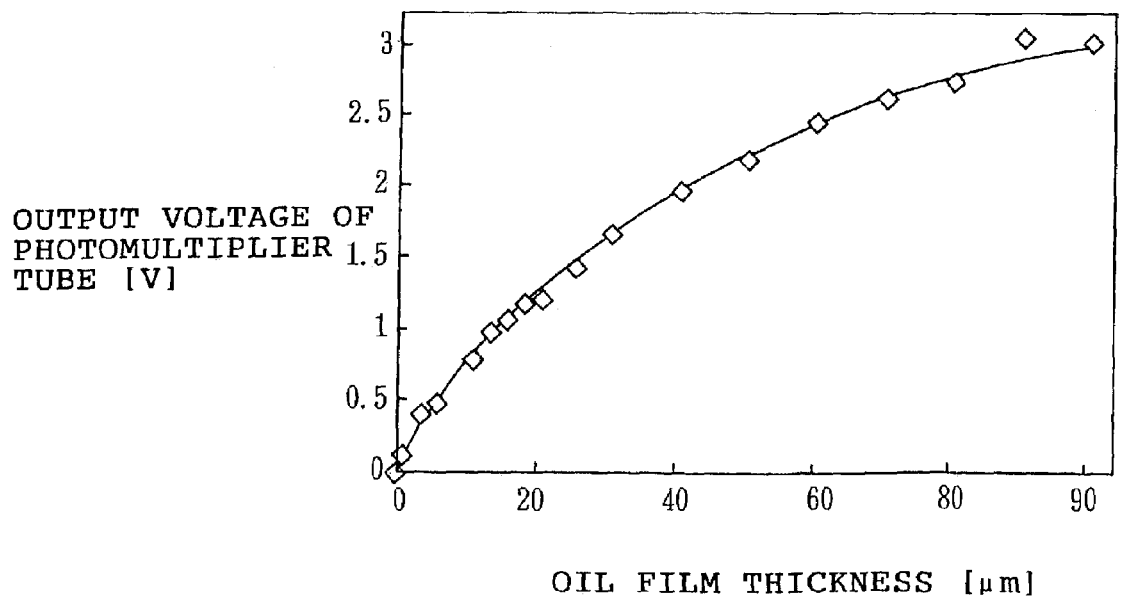
FIG. 7 is a graph showing a relationship between oil film thickness and output voltage of photomultiplier tube, showing a calibration result.

Next, the calibration method will be described with reference to FIGS. 6 and 7. As shown in FIG. 6, each oil film thickness of 0 to 100 pm was produced between the two metallic plates 9, 9, and a voltage value outputted from the photomultiplier tube 7 for each oil film thickness was used as a calibration value. Each oil film thickness was produced by using a thickness sheet 12 or plating. FIG. 7 shows a calibration result. Thereupon, by using the data shown in FIG. 7, the absolute value of oil film thickness can be measured from the output of the photomultiplier tube 7.

Figure 1:
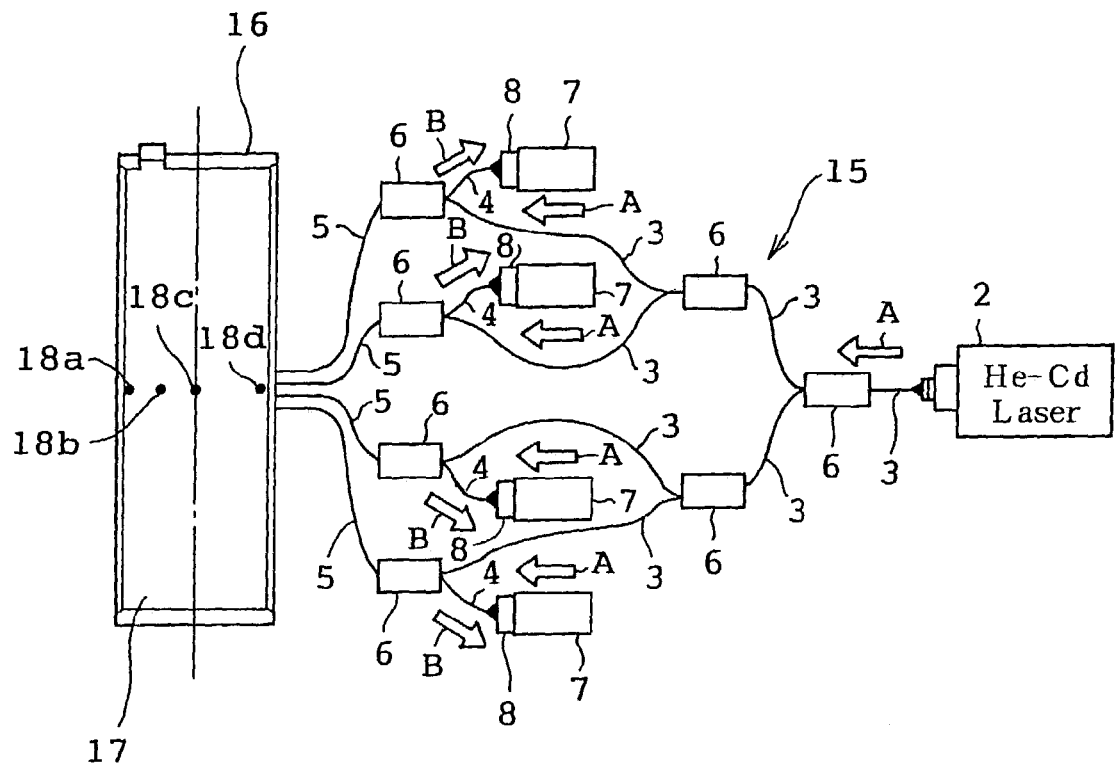
FIG. 1 is a general schematic view showing one embodiment of the present invention.

FIG. 1 shows a bearing 16 provided with an oil film thickness measuring device 15 in accordance with the present invention. Hereunder, the bearing 16 will be described. In the oil film thickness measuring device 15, the same reference numerals are applied to the same elements as those of the above-described oil film thickness measuring device 1 and the explanation thereof is omitted.

In the oil film thickness measuring device 15, one approach-route optical fiber 3 connected to a laser beam generator 2 is branched into four approach-route optical fibers 3 by three optical fiber couplers 6, and each of these four approach-route optical fibers 3 is connected with a common optical fiber 5 via an optical fiber coupler 6. Each of the four optical fiber couplers 6 connected with the common optical fiber 5 is connected with a return-route optical fiber 4, and each of these return-route optical fibers 4 is connected with a photomultiplier tube 7 via an optical filter 8.

On the other hand, the bearing 16 is formed by a half type bearing of a semicylindrical shape. A bearing body 17 of this bearing 16 is formed with sensor mounting portions 18a to 18d at four positions in the axial direction (widthwise direction of the bearing body 17), and a sensor portion 5a of the common optical fiber 5 is inserted in and connected to each of the sensor mounting portions 18a to 18d. In this case, of the four sensor mounting portions 18a to 18d, the mounting portions 18a and 18d are disposed in the left and right end portions, the mounting portion 18c is disposed in the central portion in the axial direction, and the remaining portion 18b is disposed between the left end portion and the central portion.

In the above-described configuration, a laser beam A generated from one laser beam generator 2 is branched into the four approach-route optical fibers 3, and then is applied to an oil film through the sensor portions 5a of the four common optical fibers 5. Also, fluorescence B generated by a fluorescent agent in the oil film, passing through the common optical fiber 5 and the return-route optical fiber 4, is introduced into the photomultiplier tube 7, by which an oil film thickness at each measurement point (each of the sensor mounting portions 18a to 18d) can be measured by each of the photomultiplier tubes 7.

Figure 2A:
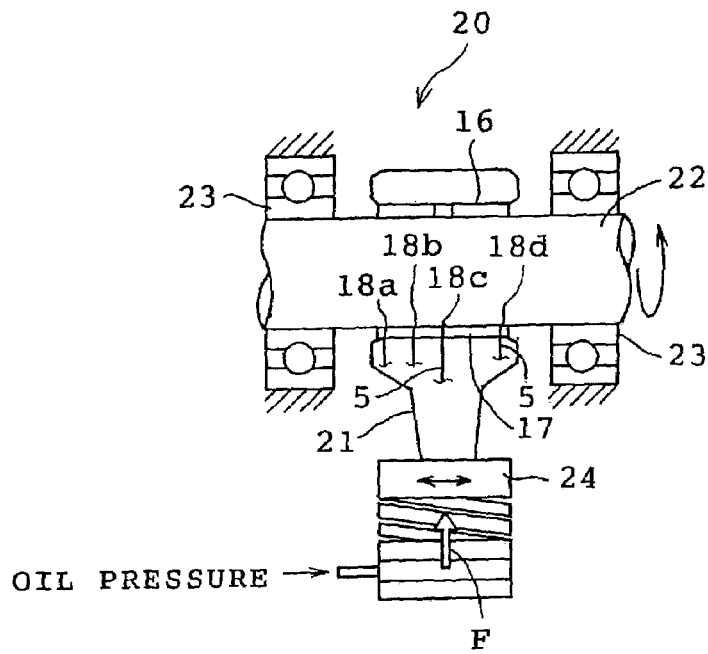
FIG. 2A is a sectional view showing an example in which a bearing is used in a state in which a bearing body is substantially parallel with a shaft.

FIG. 2A shows an example in which the abovedescribed bearing 16 is applied to a testing device 20. The bearing 16 is formed into a cylindrical shape by butting two half type bearings together, and is arranged in the inner peripheral portion of a connecting rod 21. A shaft 22 is inserted in the bearing 16, and is rotatably supported by ball bearings 23 on both sides in the axial direction. Under the connecting rod 21, a piston 24 for adjusting the position of load is disposed so that a load F due to oil pressure is applied to the bearing 16 via the piston 24 and the connecting rod 21. A lubricating oil containing a fluorescent agent is supplied to between an inner peripheral surface serving as a sliding surface of the bearing body 17 of the bearing 16 and the shaft 22, and the shaft 22 is supported by the bearing body 17 via the oil film of the lubricating oil. The sensor mounting portions 18a to 18d in the bearing body 17 are arranged in the lowermost portio in the drawing, and the configuration is such that an oil film thickness is measured at three positions of the sensor mounting portions 18a and 18d in both end portions in the axial direction and the sensor mounting portions 18c in the central portion in the axial direction.

Figure 2B:
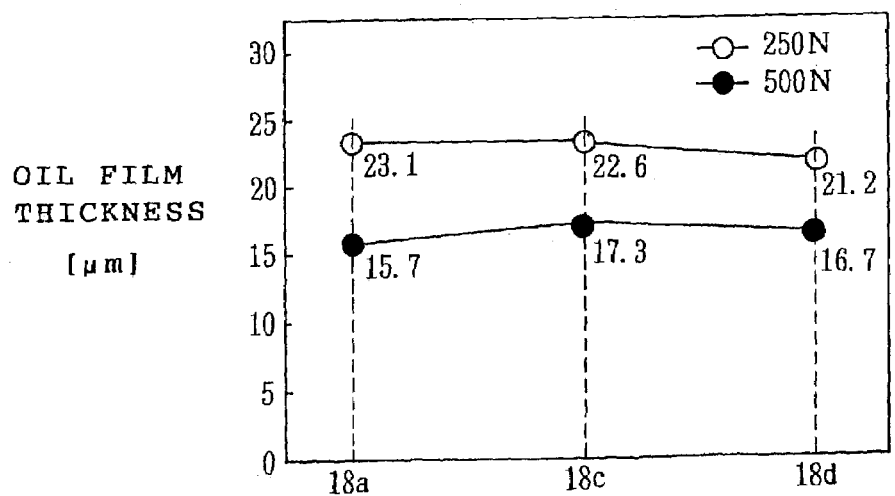
FIG. 2B is a graph showing a measurement result of oil film thickness in the example shown in FIG. 2A.
Figure 3A:
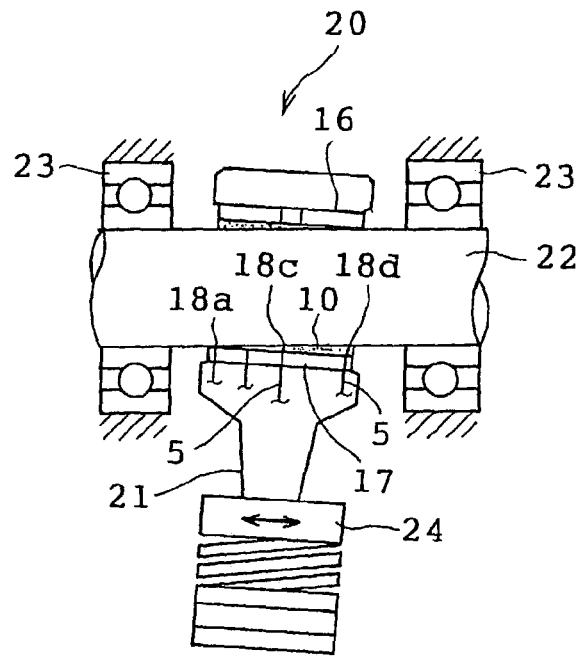
FIGS. 3A and 3B are a view and a graph corresponding to FIGS. 2A and 2B, respectively, showing an example in which a bearing is used in a state in which a bearing body is tilted with respect to a shaft 5 so as to be tilted downward to the right.
Figure 3B:
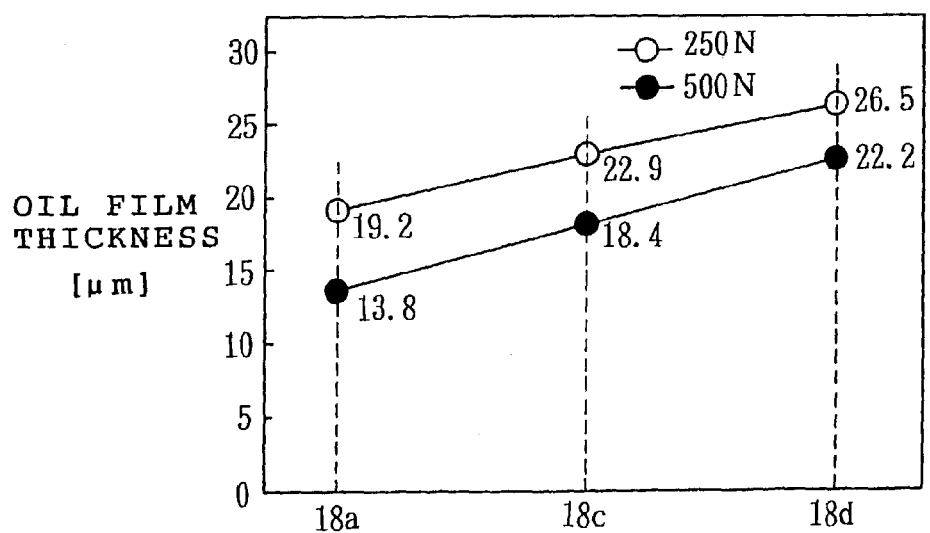
Figure 4A:
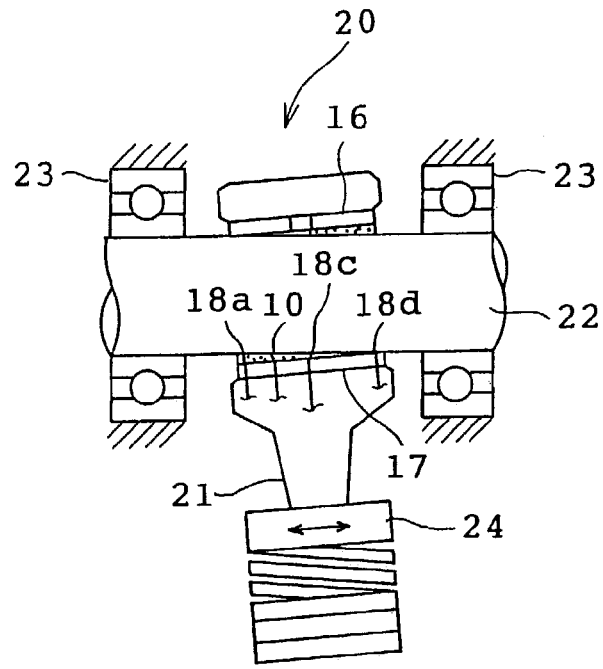
FIGS. 4A and 4B are a view and a graph corresponding to FIGS. 2A and 2B, respectively, showing an example in which a bearing is used in a state in which a bearing body is tilted with respect to a shaft so as to be tilted downward to the left.
Figure 4B:
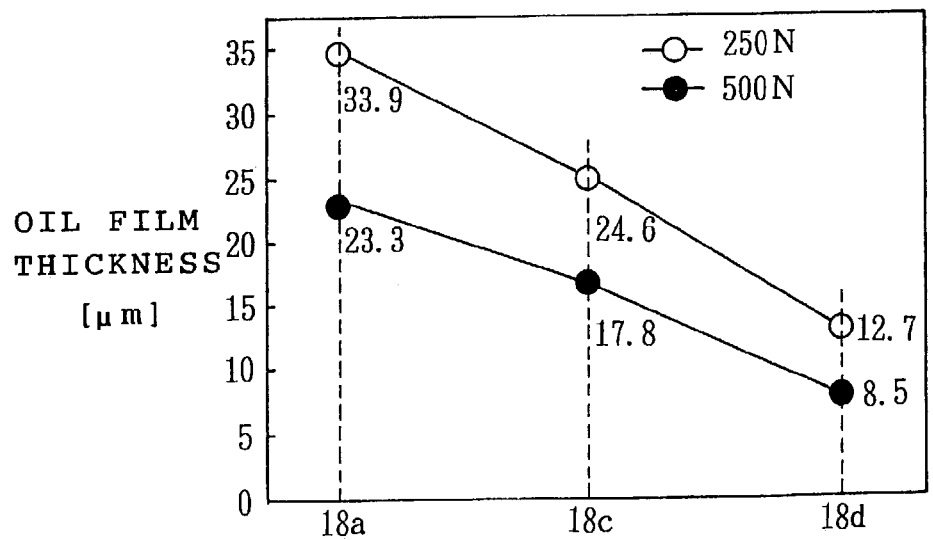

FIGS. 2A, 2B, 3 and 4 show test results. In this test, the load F applied to the bearing body 17 was set at 250 N and 500 N. In FIGS. 2A and 2B, the bearing body 17 is substantially parallel with the shaft 22. In this case, it can be seen from FIG. 2B that the thickness of oil film is approximately equal in the right and left end portions and in the central portion. FIG. 3 shows a case where the bearing body 17 is tilted with respect to the shaft 22 so as to be tilted downward to the right as shown in FIG. 3A. In this case, it can be seen from FIG. 3B that the thickness of oil film decreases from the right end portion toward the left end portion. FIG. 4 shows a case where the bearing body 17 is tilted with respect to the shaft 22 so as to be tilted downward to the left as shown in FIG. 4A. In this case, it can be seen from FIG. 4B that the thickness of oil film decreases from the left end portion toward the right end portion.

The above-described embodiment can achieve the effects as described below.

The oil film thickness measuring device 15 provided on the bearing 16 can measure the absolute value of thickness of the oil film formed on the sliding surface of the bearing body 17, and the measurement result can be utilized for the maintenance etc. of the bearing 16.

Since the oil film thickness measuring device 15 uses an optical fiber in the sensor portion, the sensor mounting portions 18a to 18d of the bearing body 17 take up less mounting space, and also the degree of freedom of mounting position is high. Further, because of transmission by light, an advantage of being not affected by electrical noise is offered.

Since the approach-route optical fiber 3 and the return-route optical fiber 4 are made common by one common optical fiber 5 at a point near each of the sensor mounting portions 18a to 18d, one common optical fiber 5 has only to be connected to each of the sensor mounting portions 18a to 18d, and thus each of the sensor mounting portions 18a to 18d can be made small as compared with a case where two optical fibers are connected.

Since the optical filter 8 that shuts off the passage of a beam other than the beam with a wavelength corresponding to the fluorescence B is provided on the inlet side of each of the photomultiplier tubes 7, only the fluorescence B generated by the fluorescent agent in the oil film is applied to the photomultiplier tube 7, so that the intensity of fluorescence can be detected properly, and hence the oil film thickness can be measured as exactly as possible.

Since the sensor mounting portions 18a to 18d are provided at a plurality of positions in the axial direction of the bearing body 17 so that the oil film thickness can be measured in these sensor mounting portions 18a to 18d, the tilting state of the bearing body 17 with respect to the shaft 22 can be detected, and the result can be utilized for the maintenance of the bearing 16.

Since the laser beam generated from one laser beam generator 2 is branched into a plurality of beams so that the oil film thickness can be measured simultaneously at a plurality of positions, the configuration can be made compact though the measurement can be made at a plurality of positions.

The present invention is not limited to only the above-described embodiment, and can be modified or expanded as described below.

The sensor mounting portions 18a to 18d may be provided in a circumferential direction of the bearing body 17 in place of being provided in the axial direction of the bearing body 17.

The sensor mounting portion may be provided at only one place on the bearing body 17.

What is claimed is:

1. A bearing with an oil film thickness measuring device, comprising:

a bearing body for supporting a shaft via an oil film; and the oil film thickness measuring device for measuring a thickness of said oil film formed on the sliding surface of said bearing body, wherein a fluorescent agent which generates fluorescence of a predetermined wavelength is mixed in a lubricating oil, and a plurality of sensor mounting portions are provided in said bearing body, and said oil film thickness measuring device comprises:

laser beam generating means for generating a laser beam with a wavelength different from the wavelength of said fluorescence;

an approach-route optical fiber having one end of which is connected to said sensor mounting portion and for applying the laser beam generated by said laser beam generating means to an oil film on said sliding surface of said bearing body;

a return-route optical fiber having one end of which is connected to said sensor mounting portion and for receiving the fluorescence generated by the fluorescent agent in said oil film according to the application of said laser beam and introducing it to the outside;

detector means for detecting a tilt state of the bearing body with respect to the shaft;

fluorescence intensity detecting means for detecting the intensity of fluorescence passing through said return-route optical fiber; and tilt measuring means for measuring the tilt state of the bearing body, wherein the oil film thickness is measured based upon a detection result of the fluorescence intensity detecting means and the measured oil film thickness is used by the tilt measuring means for measuring the tilt state of the bearing body.

2. The bearing with an oil film thickness measuring device according to claim 1, wherein an optical filter which shuts off the passage of a beam with a wavelength other than the wavelength corresponding to the fluorescence is provided on the inlet side of said fluorescence intensity detecting means.

3. The bearing with an oil film thickness measuring device according to claim 1, wherein the sensor mounting portions are provided at a plurality of positions, have a plurality of sensors in a form of optical.

4. The bearing with an oil film thickness measuring device according to claim 3, further comprising an optical filter.

* * * * *